(12) United States Patent
Shahinpoor

(10) Patent No.: US 6,464,655 B1
(45) Date of Patent: Oct. 15, 2002

(54) ELECTRICALLY-CONTROLLABLE MULTI-FINGERED RESILIENT HEART COMPRESSION DEVICES

(75) Inventor: Mohsen Shahinpoor, Albuquerque, NM (US)

(73) Assignee: Environmental Robots, Inc., Albuquerque, NM (US)

( * ) Notice: Subject to any disclaimer, the term of this patent is extended or adjusted under 35 U.S.C. 154(b) by 0 days.

(21) Appl. No.: 09/526,038

(22) Filed: Mar. 15, 2000

Related U.S. Application Data
(60) Provisional application No. 60/124,840, filed on Mar. 17, 1999.

(51) Int. Cl.$^7$ ................................................. A61H 7/00
(52) U.S. Cl. ........................................ 601/153; 600/16
(58) Field of Search .............................. 600/16, 17, 37; 623/3.1, 3.27–3.3; 601/134, 135, 152, 153

(56) References Cited

U.S. PATENT DOCUMENTS

| | | |
|---|---|---|
| 2,238,967 A | 4/1941 | Brown |
| 3,233,607 A | 2/1966 | Bolie |
| 3,279,464 A | 10/1966 | Kline |
| 3,371,662 A | 3/1968 | Heid et al. |
| 3,455,298 A | 7/1969 | Anstadt |
| 3,513,836 A | 5/1970 | Sausse |
| 3,587,567 A | 6/1971 | Schiff |
| 3,667,069 A | 6/1972 | Blackshear et al. |

(List continued on next page.)

OTHER PUBLICATIONS

Y. Wakisaka, et al., "Application of Hydrogen Absorbing Alloys to Medical Rehabilitation Equipment", IEEE Trans. on Rehabilitation Engineering, vol. 5, No. 2, pp. 148–157 (1997).

M. Shahinpoor, "Ion–Exchange Polymer–Metal Compositions as Biomimetic Sensors and Actuators", in Polymer Sensors and Actuators, edited by Y. Osada and D. DeRossii, Springer Verlag Publishing, Springer (1999).

M. Shahinpoor, Y. Bar–Cohen, J. Simpson, J. Smith, "Ionic Polymer MetalComposites (IPMC's) as biomimetic sensors, actuators and artificial muscles—a review", J. Smart Mater. Structures, vol. 7, pp. 15–30, (1998).

*Primary Examiner*—Jeffrey R. Jastrzab
*Assistant Examiner*—Frances P. Oropeza
(74) *Attorney, Agent, or Firm*—Dennis F. Armijo

(57) ABSTRACT

Soft, multi-fingered resilient robotic fingers for selectively assisting the ventricles, and in particular the left ventricle, of a weak heart to produce internal pressure and to pump blood from one or more sides, in synchrony with the natural systolic contraction of the ventricle, as well as providing arrhythmia control of a beating heart. The apparatus is microprocessor and electrically-controlled and completely implantable. The plurality of soft fingers monitor and gently squeeze the heart (systole) to enhance blood circulation and assist a weak heart. The soft fingers work in harmony, by means of a micro-processor controlled solenoid or other linear robotic actuators such as metal-hydride actuators or polymeric artificial muscles, and a resilient body or a spring, to close once the solenoid is powered electrically and quickly retract away from the heart when the solenoid is not powered. This quick opening action allows the heart to expand freely (diastole) once it is compressed to allow the blood to naturally and freely return to the heart ventricles and coronary veins. The soft fingers can be connected to each other by means of elastic membranes or skirts to provide a resilient compression cup. The structure is equipped with a flexible and undulating stem connecting the structure to the robotic actuation mechanism housed in the abdomen of the patient. Monitoring electrones can be affixed to the soft fingers. The power supply for the implanted device can be long lasting batteries that can be recharged transcutaneously.

18 Claims, 14 Drawing Sheets

U.S. PATENT DOCUMENTS

| | | |
|---|---|---|
| 3,668,708 A | 6/1972 | Tindal |
| 3,791,769 A | 2/1974 | Kovacs |
| 3,865,102 A | 2/1975 | Birtwell et al. |
| 3,915,158 A | 10/1975 | Simjian |
| 4,048,990 A | 9/1977 | Goetz |
| 4,092,742 A | 6/1978 | Kantrowitz et al. |
| 4,143,425 A | 3/1979 | Runge |
| 4,167,046 A | 9/1979 | Portner et al. |
| 4,176,411 A | 12/1979 | Runge |
| 4,192,293 A | 3/1980 | Asrican |
| 4,291,707 A | 9/1981 | Heilman et al. |
| 4,304,225 A | 12/1981 | Freeman |
| 4,448,190 A | 5/1984 | Freeman |
| 4,506,658 A * | 3/1985 | Casile .................. 128/1 D |
| 4,536,893 A | 8/1985 | Parravicini |
| 4,541,417 A | 9/1985 | Kirkorian |
| 4,583,523 A | 4/1986 | Kleinke et al. |
| 4,621,617 A | 11/1986 | Sharma |
| 4,690,134 A | 9/1987 | Snyders |
| 4,731,076 A | 3/1988 | Noon et al. |
| 4,925,443 A * | 5/1990 | Heilman et al. .............. 600/16 |
| 4,957,477 A | 9/1990 | Lundback |
| 5,081,986 A | 1/1992 | Cho |
| 5,098,369 A * | 3/1992 | Heilman et al. .............. 600/16 |
| 5,131,905 A | 7/1992 | Grooters |
| 5,150,706 A | 9/1992 | Cox et al. |
| 5,169,381 A | 12/1992 | Snyders |
| 5,250,167 A | 10/1993 | Adolf et al. |
| 5,256,132 A | 10/1993 | Snyders |
| 5,383,840 A | 1/1995 | Heilman et al. |
| 5,389,222 A | 2/1995 | Shahinpoor |
| 5,397,349 A | 3/1995 | Kolff et al. |
| 5,558,617 A | 9/1996 | Heilman et al. |

\* cited by examiner

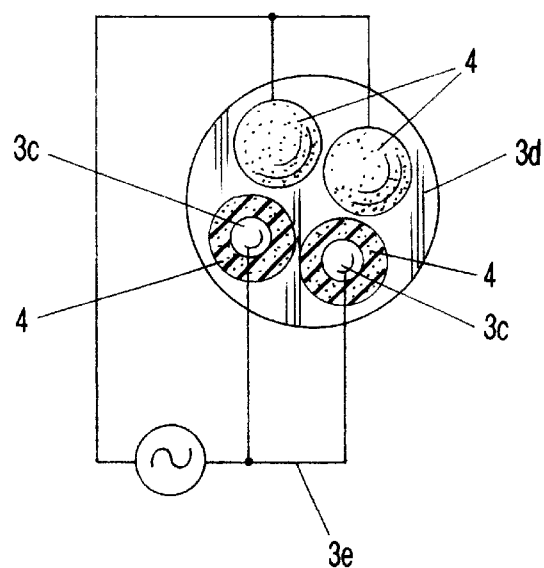
FIG-6c1
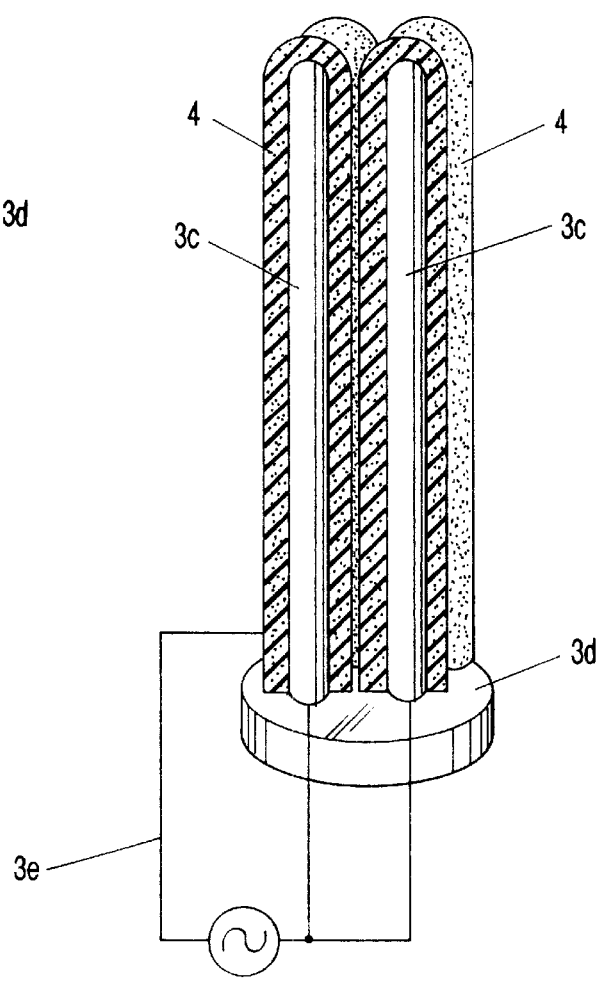
FIG-6c2

ELECTRICALLY-CONTROLLABLE MULTI-FINGERED RESILIENT HEART COMPRESSION DEVICES

CROSS-REFERENCE TO RELATED APPLICATIONS

This application is based on U.S. Provisional Application Ser. No. 60/124,840, entitled "Electrically-Controllable Multi-Fingered Resilient Heart Compression Devices", filed on Mar. 17, 1999, the teachings of which are incorporated herein by reference.

BACKGROUND OF THE INVENTION

1. Field of the Invention (Technical Field)

The present invention relates to heart compression and assist and arrhythmia control devices. More particularly the invention relates to a multi-soft fingered, resilient electrical heart compression apparatus which can be implanted external to the patient's heart for compressing a heart ventricle robotically and intelligently, which contains control means such as bradycardic (pacing) and tachyarrhythmic (cardioverting/defibrillating) to facilitate the device operation in synchronism with left ventricular contraction. The apparatus is also preferably capable of transcutaneous recharging of the implanted batteries, or can be powered by a pair of transcutaneous conducting wires by an electronic battery pack system worn around a user's waist.

2. Background Art

There presently exists no implantable heart compression device to help patients suffering from congestive heart failure (CHF), a progressive disease often precipitated by acute myocardial infarction. All artificial heart or left ventricular assist devices have either not worked in the past or are just temporary solutions for patients needing a donor heart for transplant. Existing devices generally feature blood flow pathways made from non-biological materials that often damage blood cells and blood proteins and produce clots, thereby presenting a generic risk thromboembolism in the circulatory system. In fact, blood clots cause most of the deaths reported after implantation of an artificial heart or assist device. The majority of these patients have a normal right ventricle; however, most have a left ventricle that has been damaged in specific regions. Therefore, there is a need for a heart compression device designed to assist the weak muscles of a failing heart that augments the heart's pumping power. This device could also incorporate pacemaker and implantable cardioverter/defibrillator technology for treating patients who also suffer from such electrical dysfunctions as bradycardia or tachyarrhythmias. Current Left Ventricular Assist Device (LVAD) devices are heavy and generally have to be attached to a cart to be dragged around by the patient. In addition, they lack a satisfactory implantable energy source, requiring patients to be constantly tethered to an external power source. Previous attempts to provide ventricular assistance have ranged from artificial hearts (e.g., the Jarvik-7), to devices which directly pump the blood, via an artificial pathway inserted through the ventricular wall to devices which exert pressure on the outside of the heart. Historically, heart-compression devices involve some form of flexible bladder within a support structure such that expansion of the bladder presses on the ventricle and facilitates expulsion of blood. These types of devices are disclosed in U.S. Pat. No. 3,587,567 to Schiff; U.S. Pat. No. 3,371,662 to Heid et al.; U.S. Pat. No. 4,048,990 to Goetz; and U.S. Pat. No. 4,192,293 to Asrican. U.S. Pat. No. 4,506,658 to Casile discloses a truncated conical structure of sac-lined rigid panels separated by contractible and expandable sections. Another type of cardiac assist system is designed to compress all or part of the heart by alternately tightening and releasing a circumferential compression band. For example, U.S. Pat. No. 4,304,225 to Freeman teaches the use of a flexible strap which is fixed to a contoured plastic block and which would pass across the back of the heart. In response to electrical pulses, a motor assembly alternately reels in and releases the flexible strap, thereby forcing fluid from the organ. This prior art device is ineffective because a pressure of between 20 and 70 mm Hg in the volume under the strap pumps blood from the right ventricle but not the left, since 70 mm Hg or more is required for blood to exit the left ventricle into the aorta. Freeman also discloses the use of a tubular compression sleeve that substantially encircles the heart and which comprises a series of interconnected expandable elliptical chambers. In use, a liquid solution is pumped into the sleeve from a supply chamber, causing the elliptical chambers to expand radially inward to compress the heart in its systolic phase. The solution then is released from the sleeve back to a supply chamber, permitting the heart to expand in its diastolic phase. These bladder-type devices can lead to a buildup of blood in the lungs, producing pulmonary complications. U.S. Pat. No. 4,583,523 to Kleinke and Freeman illustrates another prior art heart assist mechanism. This device compresses the aorta, not the left ventricle, and it compresses during the diastolic phase of cardiac contraction instead of the systolic phase. There is no means to monitor the adequacy of left ventricular stroke volume.

U.S. Pat. No. 4,925,443 to Marlin S. Heilman and Steve A. Kolenik, discloses an implantable ventricular assist device which includes, (1) one or more movable compression assemblies for engaging a ventricle of the heart; (2) an operating mechanism for cyclically actuating the movable compression assemblies and thereby alternately ejecting blood from the ventricle and permitting the ventricle to refill; (3) a sensing means to detect adequacy of ventricular stroke volume and/or pressure; (4) a control mechanism to assure adequate ventricular stroke volume by regulating the compressive force of the compression assemblies, and also to control pacemaker, cardioverter/defibrillator, and recorder subsystems; and (5) an electrical power source.

To prevent the edges of the compression assembly pressure plates from creating pressure points which might cause possible damage to the heart, a related continuation-in-part patent, U.S. Pat. No. 5,098,369, to Marlin S. Heilman, et al., discloses replacing the contact pad of each compression assembly with a gel-filled contact pad of special construction that compresses the heart ventricle more uniformly without damaging the ventricle. Another related patent, U.S. Pat. No. 5,098,369, to Heilman, et. al., discusses a ventricular assist device for a heart which includes a compression band-stay-pad assembly for encircling substantially the entire heart perimeter and comprising an elongated band member or chain disposed in a sealed protective structure filled with a lubricating medium.

Yet another related patent, U.S. Pat. No. 5,558,617, to Heilman, et. al, discusses a ventricular assist device for a heart including a compression band-stay-pad assembly for encircling substantially the heart perimeter and comprising an elongated band member or chain disposed in a sealed protective structure filled with a lubricating medium. The band member is fixed at one end and wound upon, or unwound from, a rotatable spool by a drive motor through a speed reducer.

Other previous attempts to provide ventricular assistance have ranged from artificial hearts (e.g., the Jarvik-7), to devices which directly pump the blood via an artificial pathway inserted through the ventricular wall, to devices which exert pressure on the outside of the heart. Most frequently, these latter pressure-exerting devices involve some form of flexible bladder within a support structure such that expansion of the bladder presses on the ventricle and facilitates expulsion of blood. These types of devices are disclosed in U.S. Pat. No. 3,233,607 to Bolie; U.S. Pat. No. 3,279,464 to Kline; U.S. Pat. No. 3,587,567 to Schiff; U.S. Pat. No. 3,371,662 to Heid et al.; U.S. Pat. No. 4,048,990 to Goetz; U.S. Pat. No. 4,192,293 to Asrican; U.S. Pat. No. 3,455,298 to Anstadt; U.S. Pat. No. 4,690,134 to Snyder; U.S. Pat. No. 5,169,381 to Snyder; U.S. Pat. No. 5,256,132 to Snyder; U.S. Pat. No. 4,731,076 to Noon et al.; and U.S. Pat. No. 4,957,477 to Lundbäack. U.S. Pat. No. 4,506,658 to Casile discloses a truncated conical structure of sac-lined rigid panels separated by contractible and expandable sections. U.S. Pat. No. 4,621,617 to Sharma shows another similar device which is electromagnetically controlled and comprises a pair of hinged compression members. Further, U.S. Pat. No. 4,536,893 to Parravicini teaches using two segmented sacs, selectively fed by a pumping fluid to compress the right and left ventricles separately. In general, bladder systems have various shortcomings. These include the possibility of catastrophic bladder fluid leakage (as a result of the fluid pressures involved), a propensity for damaging the heart surface due to poor fixation and/or rubbing of the bladder against the heart's surface, and the unnatural convex form presented to the heart's surface during systolic bladder expansion. U.S. Pat. No. 4,583,523 to Kleinke and Freeman illustrates a heart assist mechanism that compresses the aorta, rather than a ventricle, and it compresses during the diastolic phase of cardiac contraction instead of the systolic phase.

Other prior art references of relevance to the present invention are:

U.S. Pat. No. 5,250,167 to Adolf, et al., and U.S. Pat. No. 5,389,222 to Shahinpoor in connection with electrically controllable polymeric actuators;

Y. Wakisaka, et al., "Application of Hydrogen Absorbing Alloys to Medical and Rehabilitation Equipment", IEEE Trans. on Rehabilitation Engineering, Vol. 5, No. 2, pp. 148–157 (1997);

M. Shahinpoor, "Ionic Polymer Metal Composition as Biomimetic Sensors and Actuators", in Polymer Sensors and Actuators, edited by Y. Osada and D. DeRossii, Springer-Verlag Publishing, Springer (1999); and M. Shahinpoor, Y. Bar-Cohen, J. O. Simpson, J. Smith, "Ionic Polymer Metal Composites (IPMC's) as Biomimetic Sensors, Actuators and Artificial Muscles—a Review", J. Smart Mater Structures, Vol. 7, pp 15–30 (1998).

SUMMARY OF THE INVENTION (DISCLOSURE OF THE INVENTION)

This invention comprises an implantable and entirely electrically-controlled external heart compression apparatus in the form of soft, multi-fingered resilient robotic hands for selectively assisting the ventricles, and in particular the left ventricle, of a weak heart to produce more internal pressure and to pump blood from one or more sides in synchrony with the natural systolic contraction of the ventricle. In addition, a number of methods for externally compressing a heart is included. The preferred apparatus also provides arrhythmia control of the beating heart and is powered by a robotic solenoid actuator or similar robotic actuation mechanism, including robotic metal hydride actuators as well as electroactive polymeric artificial muscles. Each of these apparatuses is for cyclically actuating the resilient compression soft fingers, thereby cyclically pumping blood from the ventricles and allowing the ventricles to refill. These apparatuses are completely implantable in the body of a patient external of the heart, thereby avoiding thrombogenesis and other complications that may arise from contact between the blood flow and artificial, nonbiological surfaces. The plurality of soft fingers comprise suitably located electrodes for heart monitoring purposes to determine the ventricular stroke volume and/or pressure. Specifically, the apparatus provides for an entirely electrically-controllable and microprocessor-controlled multi-fingered resilient sphinctering heart-compression that can be implanted inside the ribcage of a patient with a weak heart and gently squeeze the weak heart (systole) to enhance blood circulation and assist the weak heart. These apparatuses are comprised of a specially designed assembly of soft fingers that work in harmony, by means of a micro-processor controlled solenoid or other linear robotic actuators, and a resilient body or a spring, to close once the robotic solenoid is powered electrically. The apparatus is designed to be normally open (not compressing) when there is no power to the robotic solenoid or actuator. The assembly is spring loaded so that when power is removed, the fingers immediately spring open. This apparatus operates like the fingers of a hand to squeeze a weak heart (systole) but otherwise to quickly retract and stay open and away from the heart in an idle manner if the robotic actuation means is not powered. This quick opening action allows the heart to expand freely (diastole) once it is compressed to allow the blood to naturally and freely return to the heart ventricles and coronary veins. External pressure by the myocardium during ventricular systole compresses the heart muscle (myocardium) and decreases blood flow to the coronary veins that feed the heart even though the aortic pressure is increased. Thus, more than 70 percent of the coronary arterial flow occurs during diastole. The multi-fingered configuration may also have the soft fingers connected to each other by elastic membranes, bladders or skirts to provide a resilient, multi-fingered compression cup as well. In one embodiment of the invention the multi-fingered compression apparatus is equipped with a long slender and flexible and undulating stem connecting the multi-fingered compression structure to the robotic actuation mechanism housed in the abdomen of the patient. In another embodiment of the invention, an assembly of electroactive polymer fingers or patches are sutured to the myocardium and are directly electrically flexed to squeeze the heart. Yet in another embodiment of the invention, an assembly of bladder-like fingers is inflated by hydrogen gas from an electrically controlled metal-hydride actuator to create compression of the heart. The preferred embodiment of robotic actuator is a solenoid for its quick action and retraction. However, alternatively, linear motors or robotic actuators as well as robotic metal hydride actuators and polymeric artificial muscles can also be used. The power supply for the implanted apparatus can be long lasting batteries that can be recharged transcutaneously, and various other components of the apparatus can be noninvasively computer-programmed and interrogated by external circuits. The entire apparatus can be implanted endoscopically or through the abdomen of the patient rather than opening of the patient's chest. The power and electronic control means may also be placed outside the body, around the waist of the person, and directly connected by means of conducting wires through sutured conduits to the implanted apparatus.

A primary object of the present invention is to provide a weak heart, a family of new heart assist devices that are robotically computer controllable and implantable in the patient's body external to the heart, that are further, compact and light-weight.

A further object of the invention is to provide selective compression of different parts of the heart or thoracic aorta in synchrony and harmony with the natural systolic and diastolic motions of the heart.

Yet another object of the present invention is to provide an endoscopically implantable selective heart compression device equipped with built-in robotic metal hydride actuators that are electronically computer controllable.

Yet another object of the present invention is to provide an endoscopically implantable selective heart compression device equipped with robotic electroactive polymeric muscles that are electrically computer controllable.

A primary advantage of the present invention is to provide selective compression of different parts of the heart and thoracic aorta by means of specially contoured soft resilient fingers.

Yet another advantage of the present invention is to provide the heart with complete lateral and twist motions, while engaged in compression of the weak heart, by means of a flexible stem.

A further advantage of the present invention is to provide a patient with a weak heart an totally endoscopically implantable, multi-fingered compression device equipped with built-in metal hydride actuators for pneumatic computer-controlled compression of the heart.

Yet another advantage of the present invention is to provide a patient with a weak heart an endoscopically implantable, multi-fingered compression device equipped with electroactive polymeric artificial muscles which are robotically computer controllable.

Other objects, advantage and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIG. 6(c1) is a cross sectional view of the embodiment in FIG. 6(b) in a collapsed configuration allowing endoscopic insertion of the device inside a patient's ribcage;

FIG. 6(c2) is a side view of the embodiment in FIG. 6(b) in a collapsed configuration allowing endoscopic insertion of the device inside a patient's ribcage;

DESCRIPTION OF THE PREFERRED EMBODIMENTS (BEST MODES FOR CARRYING OUT THE INVENTION)

Figure 1:
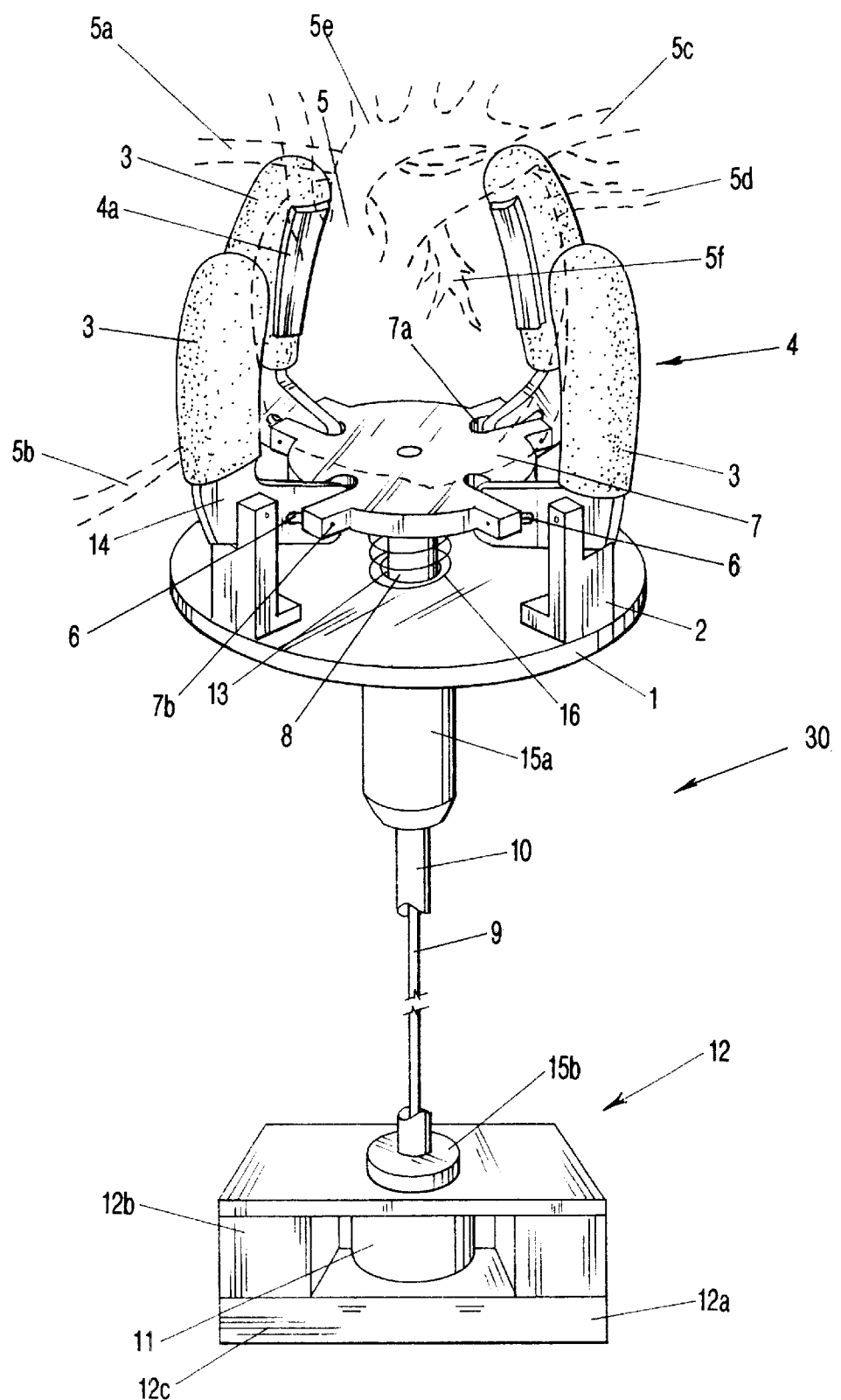
FIG. 1 is a perspective view of a preferred embodiment of the invention.

FIG. 1 shows the preferred embodiment of the present invention. Heart 5, (cardiac muscle) is being compressed by a plurality of soft compression fingers 3, each finger 3 containing a soft outer cover 4. FIG. 1 shows the associated major arteries and veins such as the superior vena cava 5(a), the inferior vena cava 5(b), the pulmonary artery 5(c), the pulmonary vein 5(d) and the aorta 5(e) as well as the coronary arteries 5(f). The multi-fingered soft and resilient robotic heart-compression devices equipped with a flexible stem 10 include soft compression fingers 3 equipped with a soft outer cover 4 that surround heart 5. The soft outer cover 4 is preferably made from soft spongy silicon rubber and can also be in the form of polymer gels or water-filled bladders. Each finger 3 is preferably equipped with pressure monitoring electrodes 4(a) for monitoring the compression of the cardiac muscle 5 to simulate normal pumping action of the myocardium muscle. The preferred apparatus comprises a central platform 7 and a support column 2 mounted on a base platform 1 to enable soft compression fingers 3 to pivotally move in harmony about hinge 14, such pivoting actions are allowed by finger slot 6, the central platform slot 7(a) and central platform pin 7(b) as well as the pulling action of cable 9 inside a cable guide (the flexible stem) 10 linearly actuating the central platform stem 8 through the support platform cylindrical slot 13. The actuation cable 9 is activated by robotic linear actuation mechanism 11 housed inside the abdomen base support assembly 12.

Figure 2:
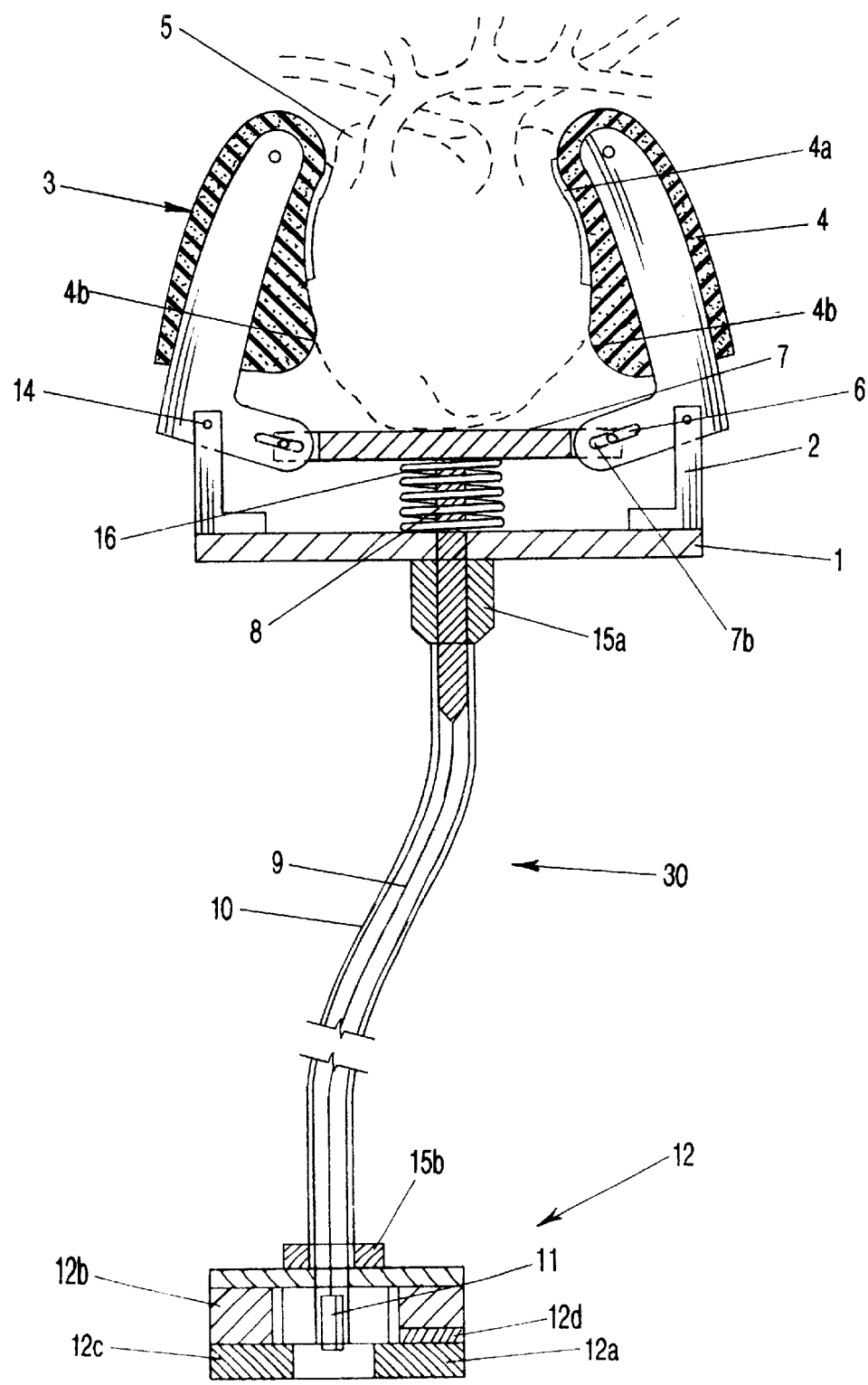
FIG. 2 is a schematic diagram of the preferred embodiment as shown in FIG. 1 showing the undulation role of the flexible stem and more detailed drawings of the compression fingers as well as schematically illustrating the exemplary control means and actuating means for the invention.

FIGS. 1 and 2 also show that the preferred heart compression assembly 30 is also equipped with support washers 15(a) and 15(b) to stabilize the laterally flexible but longitudinally inflexible cable guide 10 or the stem to allow free undulation of the stem in the presence of a resilient (spring-loaded) collar 16. Upon compression of the heart 5, the potential energy stored in the resilient collar 16 will quickly retract soft compression fingers 3 upon completion of the compression cycle to allow the diastolic expansion of heart 5 to proceed with no obstruction and to completely release heart 5 from the soft compression fingers 3 in case of any breakdown of the heart compression assembly. In the preferred embodiment, all components are preferably fabricated from bio-compatible materials and are all operating below the endurance limit of the materials to make sure no fatigue failure of any component occurs under such oscillatory loading/unloading cycles. The preferred compression assembly 30 further includes a control structure 12(b) and 12(c) that are well known in the art for electromagnetically controlling the operation of heart compression assembly as well as to monitor the actual pressure applied to the cardiac muscles 5. As shown in FIG. 2, the soft compression fingers can also have finger bumps 4(b) to enhance localized compression of ventricles. Base support assembly 12 houses a power source for the device, such as at least one long lasting battery 12(a), which can be transcutaneously recharged from outside the patient's body (not shown). Within the base support assembly 12 is control circuitry 12(b) which preferably includes a microprocessor for the robotic actuations of the linear actuator 11, to preferably provide a pulsating current of the order of 50 to 200 pulses per minute to correspond with the natural pulsations of heart 5. The base support assembly 12 can also have the microprocessor trigger the sino-atrial (SA) or atrio-ventricular (AV) nodal activity of the heart 5.

Figure 3:
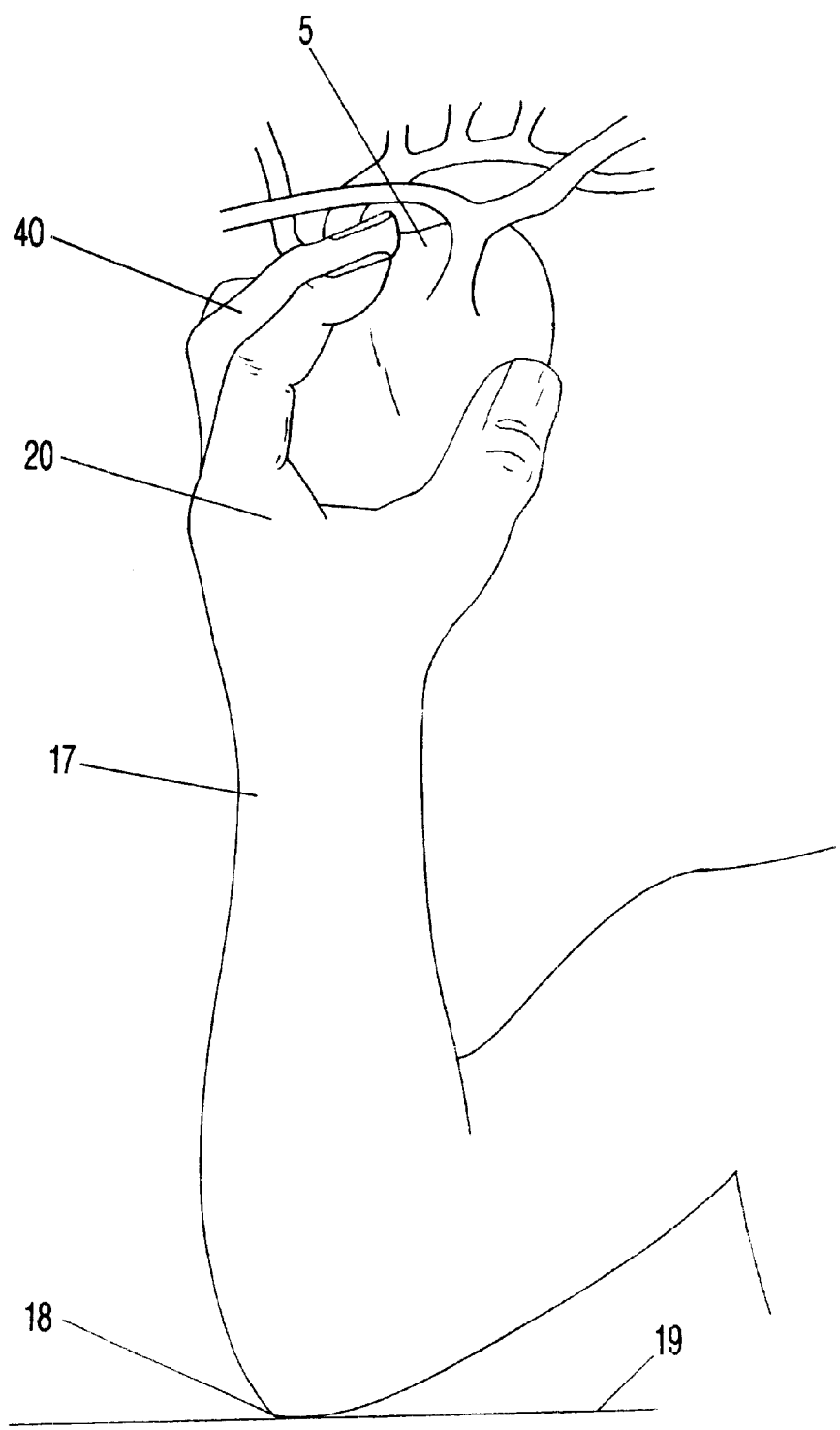
FIG. 3 is a view showing the similarity of the operation of said apparatuses and invention to an arm and hand resting on its elbow on a support surface and squeezing a heart.

FIG. 3 demonstrates how the preferred embodiment functions similarly in the from of a human arm 17 resting on its elbow 18 on a platform 19 and holding the heart 5 in a hand 20 between the human fingers 40 of hand 20 and squeezing and releasing the heart muscle 5.

Figure 4:
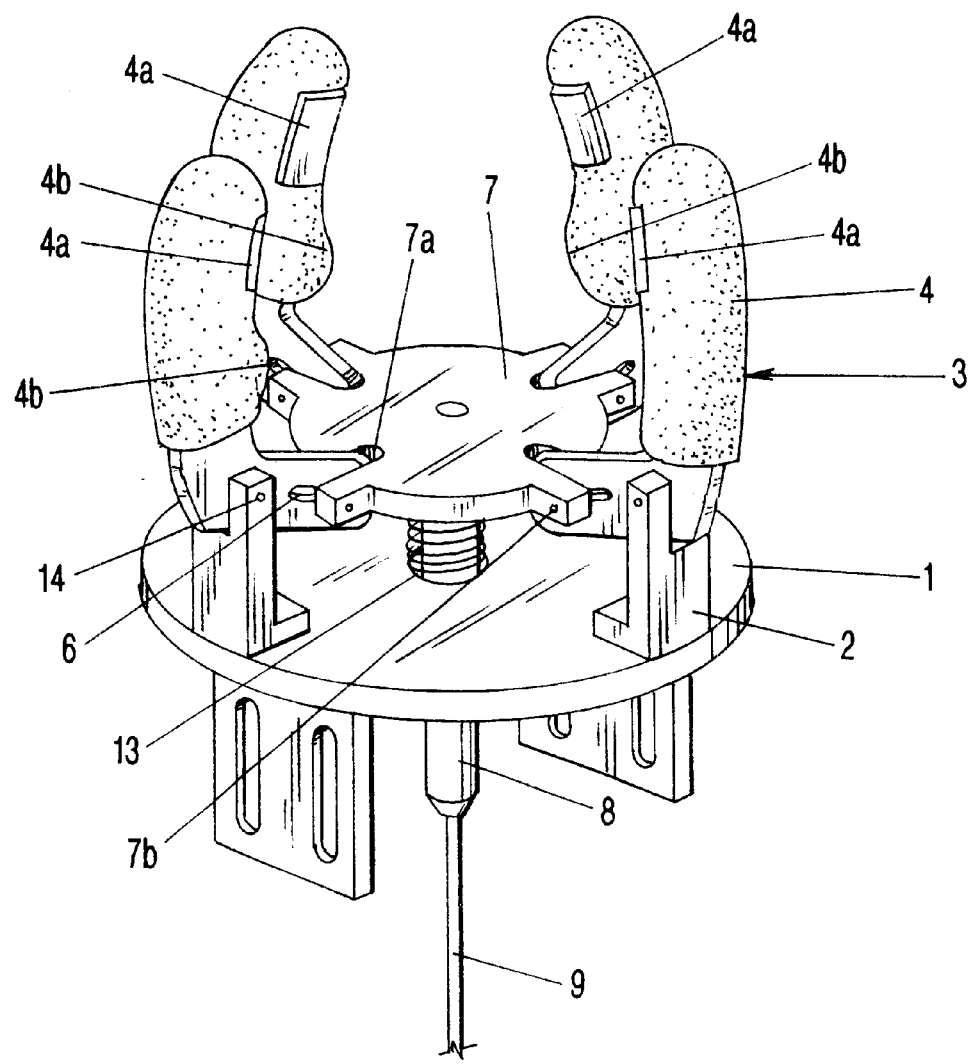
FIG. 4 is a schematic illustration of another embodiment of the compression fingers without the supporting structure and the stem.

FIG. 4 depicts an alternative embodiment without the exemplary undulating supporting stem 10 in FIGS. 1 and 2, showing the central platform 7, the base platform 1, finger support column 2, soft compression fingers 3, soft outer cover 4, sensing electrodes 4(a), soft finger bumps 4(b), central platform stem 8, actuating cable 9, finger slot 6, pivoting hinge 14, central platform slot 7(a), and central platform pins 7(b), as well as base platform bushing slot 13, for supporting the compression device within the mammalian body.

Figure 5A:
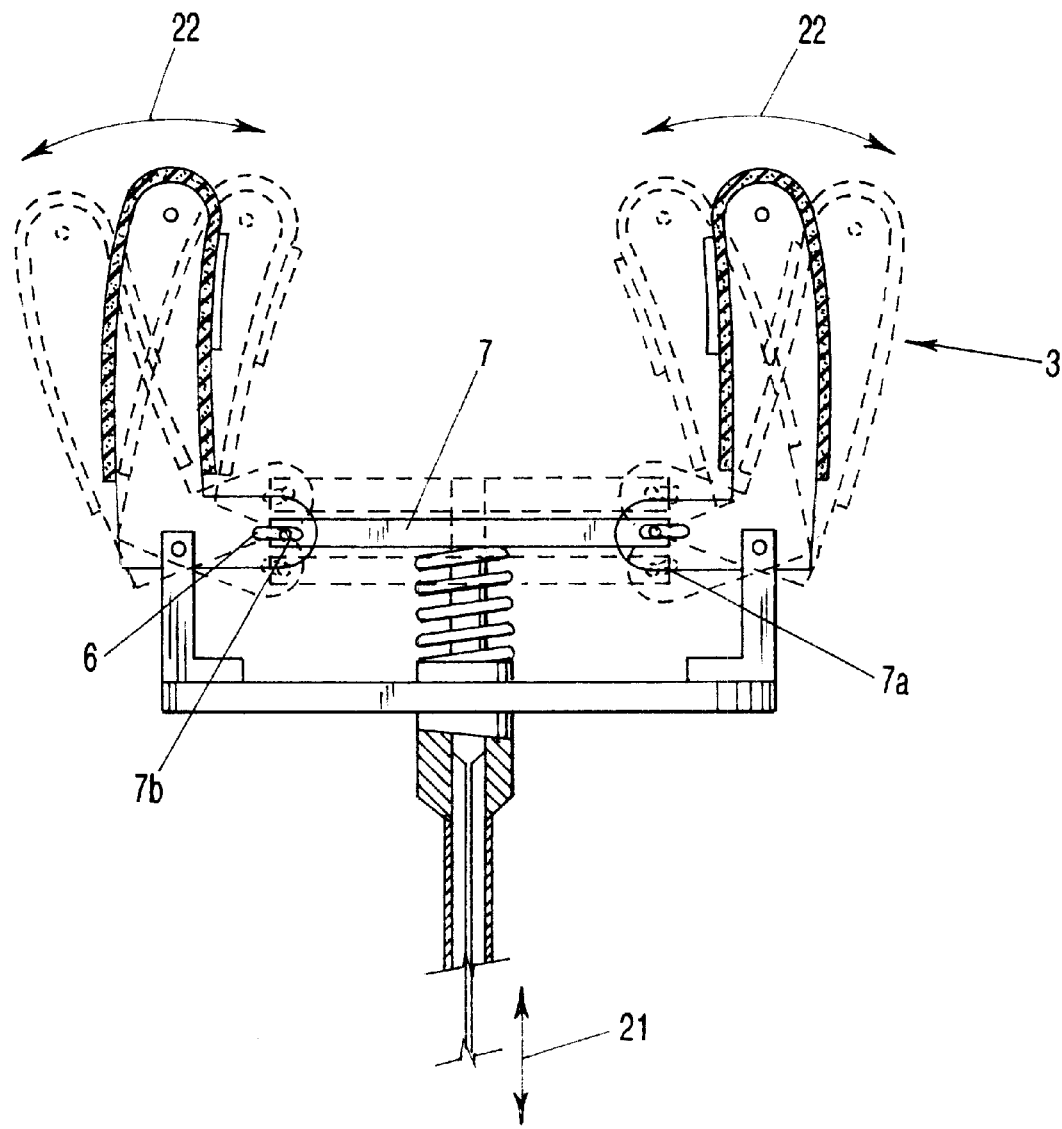
FIG. 5(a) illustrates the operation of the compression fingers due to linear motion of the spindle and the effect of the two pivotal hinges and a slot in the base of the fingers.

FIG. 5(a) shows how the soft compression fingers 3 function in the preferred embodiment. Soft compression fingers 3, central platform slot 7(a), finger slot 6, and central platform pin 7(b), allow the linear motion 21 of the central platform 7 to be converted to radial swinging motion 22 of the soft compression fingers 3, as shown.

Figure 5B:
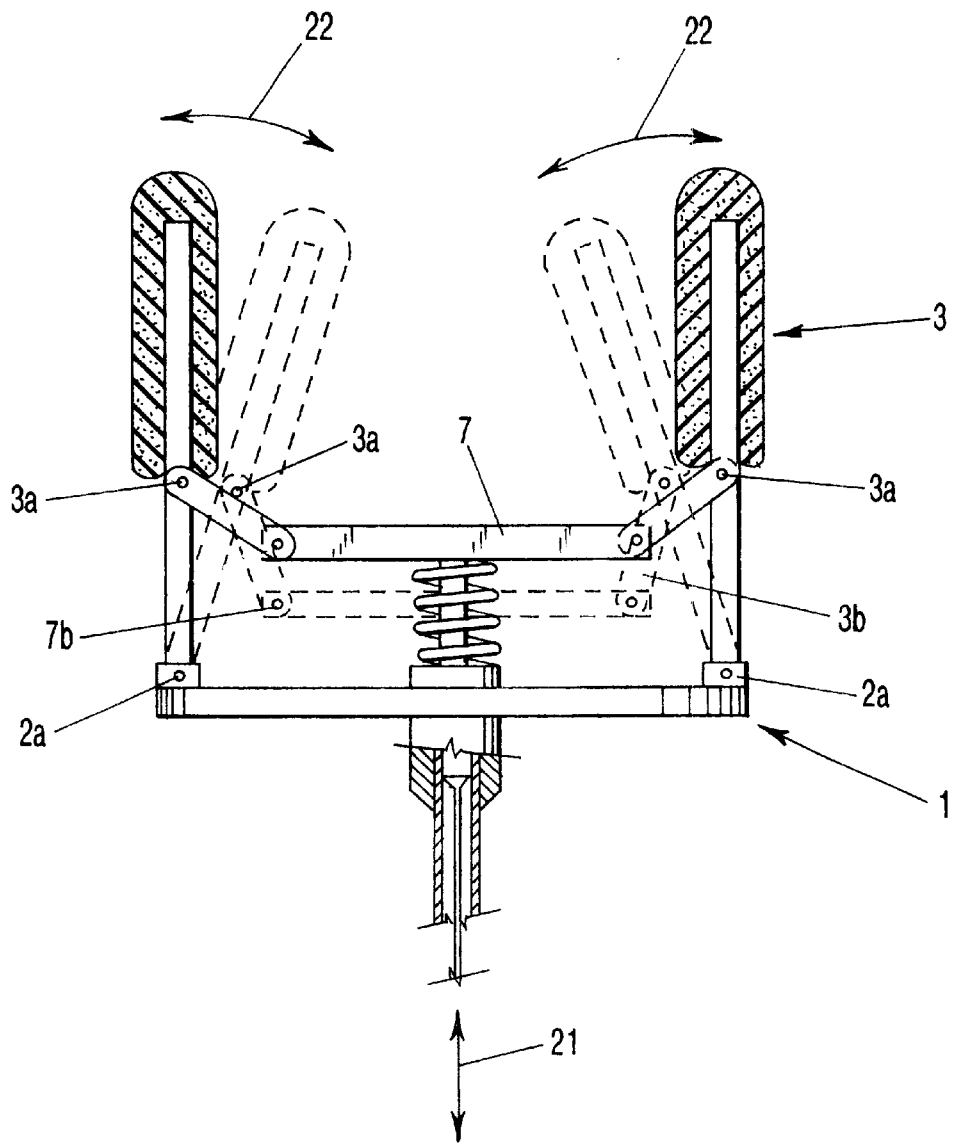
FIG. 5(b) illustrates the operation of the compression fingers due to linear motion of the spindle, and the effect of the three pivotal hinges and no slot in the base of the fingers.

FIG. 5(b) depicts another embodiment of the arrangement of soft compression fingers 3 for the conversion of linear robotic actuator motion to radial swinging motion of the soft compression fingers 3. In this embodiment there is no central platform slot in conjunction with two hinges 7(a) and 14 but three hinges 2(a), central platform pin 7(b) and 3(a), as well as a connecting link 3(b) to allow the linear motion 21 of the central platform 7 to be converted to the swinging radial motion 22 of the soft compression fingers 3.

Figure 6A:
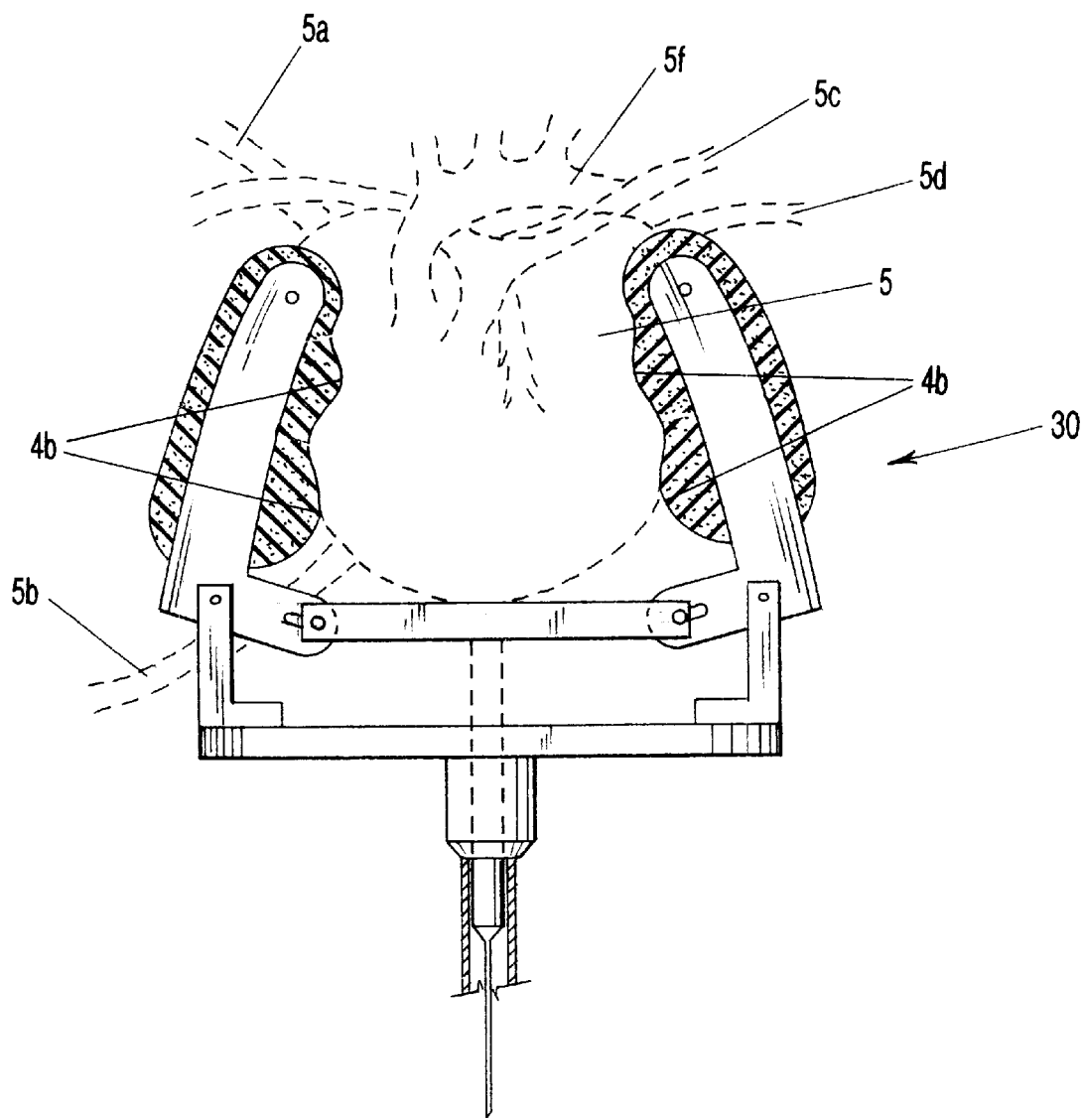
FIG. 6(a) depicts the arrangement of the soft finger bumps and the pressure sensors to selectively compress different parts of the heart and sense the imparting compression pressure.

FIG. 6(a) depicts compression assembly 30, compressing heart 5, and the associated main arteries and veins 5(a), 5(b), 5(c), 5(d), 5(e), and 5(f) in the presence of finger bumps 4(b) to selectively apply compression to various regions of the myocardium and arteries and veins as the need arises.

Figure 6B:
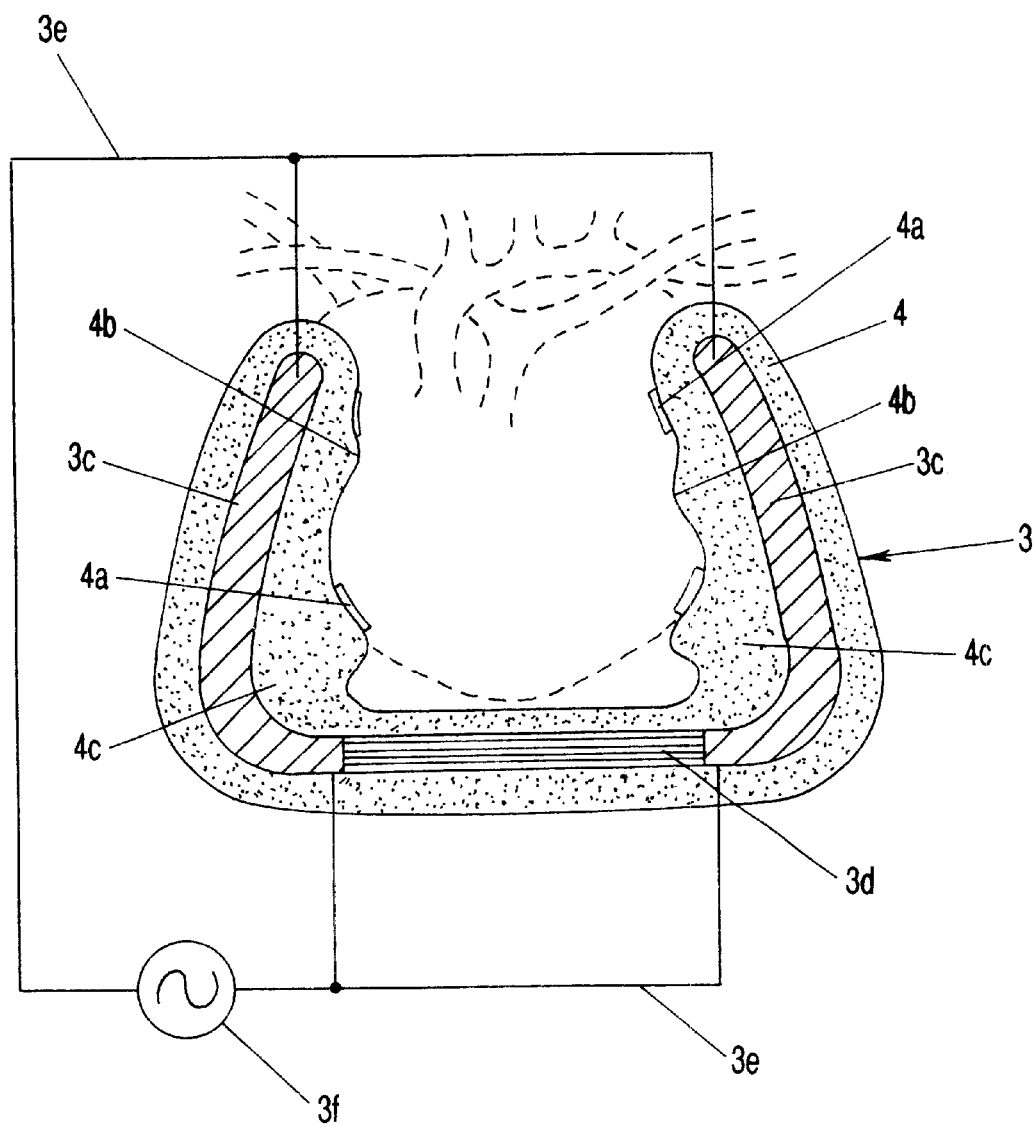
FIG. 6(b) depicts another embodiment of the compression device using collapsible multi-fingered metal-hydride finger actuators.

FIG. 6(b) depicts another preferred embodiment of the compression assembly 30 in the form of collapsible assembly of fingers, made with a metal hydrice hydrogen sponge such as LaNi, TiFe, MgNi, and TiMn groups, encapsulated by bladder-type contourable and inflatable fingers 4 that can be inflated by hydrogen gas 4(c) While still equipped with sensors 4(a) and bump 4(b). In this embodiment, Peltier thermoelectric cells 3(c) may be used to heat and cool the fingers to cause them to desorb or absorb hydrogen gas into the fingers, thus providing cyclic compression of the heart by means of the power source 3(f) via conducting wires 3(e). The metal hydride fingers in this embodiment are connected to each other by a collapsible base 3(d).

FIGS. 6(c1) and 6(c2) depict another preferred embodiment of FIG. 6(b) in a collapsed configuration allowing endoscopic insertion of the device through a cannula inside a patient's ribcage. Note that in this embodiment the flexible base 3(d) can be folded in a tubular configuration.

Figure 6D:
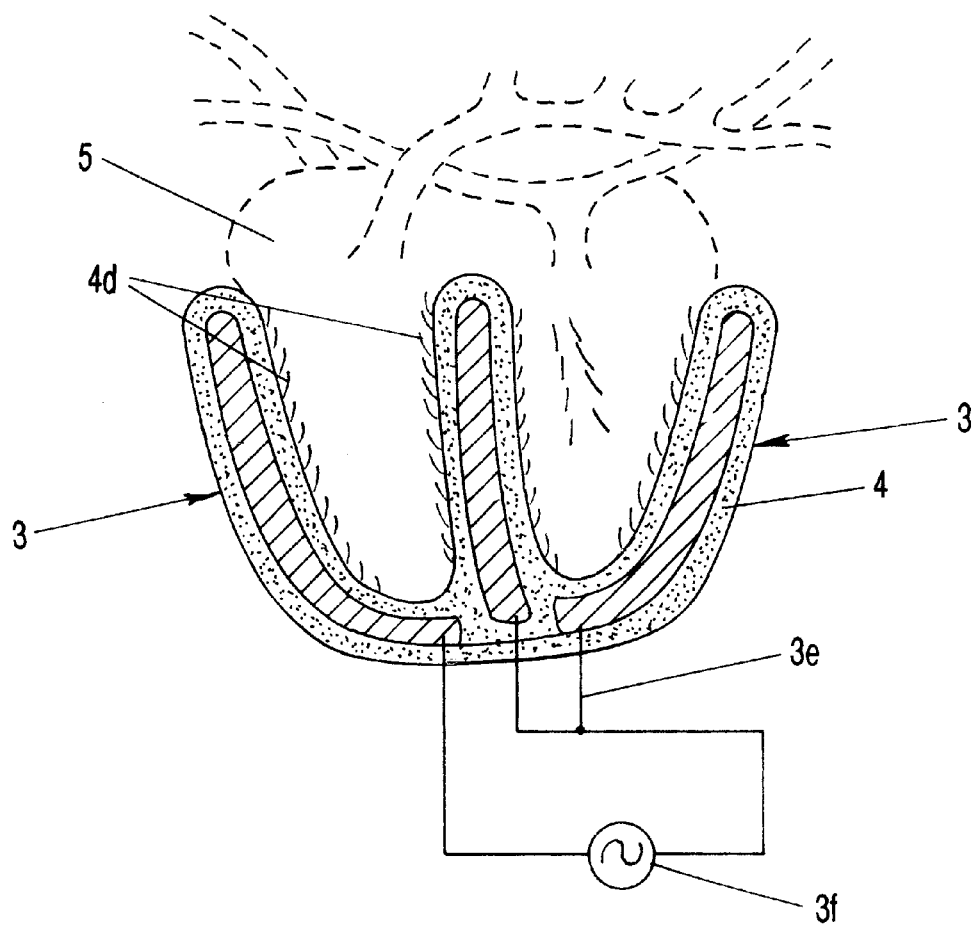
FIG. 6(d) depicts another embodiment of the invention using artificial muscles.

FIG. 6(d) depicts another preferred embodiment of the invention in the form of collapsible and endoscopically implantable assembly of soft fingers 3 made with electro-active polymer sensors and actuators that can be directly electrically powered and computer-controlled by wires 3(e) and power source 3(f). In this preferred embodiment, the polymeric artificial muscles can be sutured or bonded to the myocardium 5 by suturing methods 4(d) known to those skilled in the art.

Figure 7:
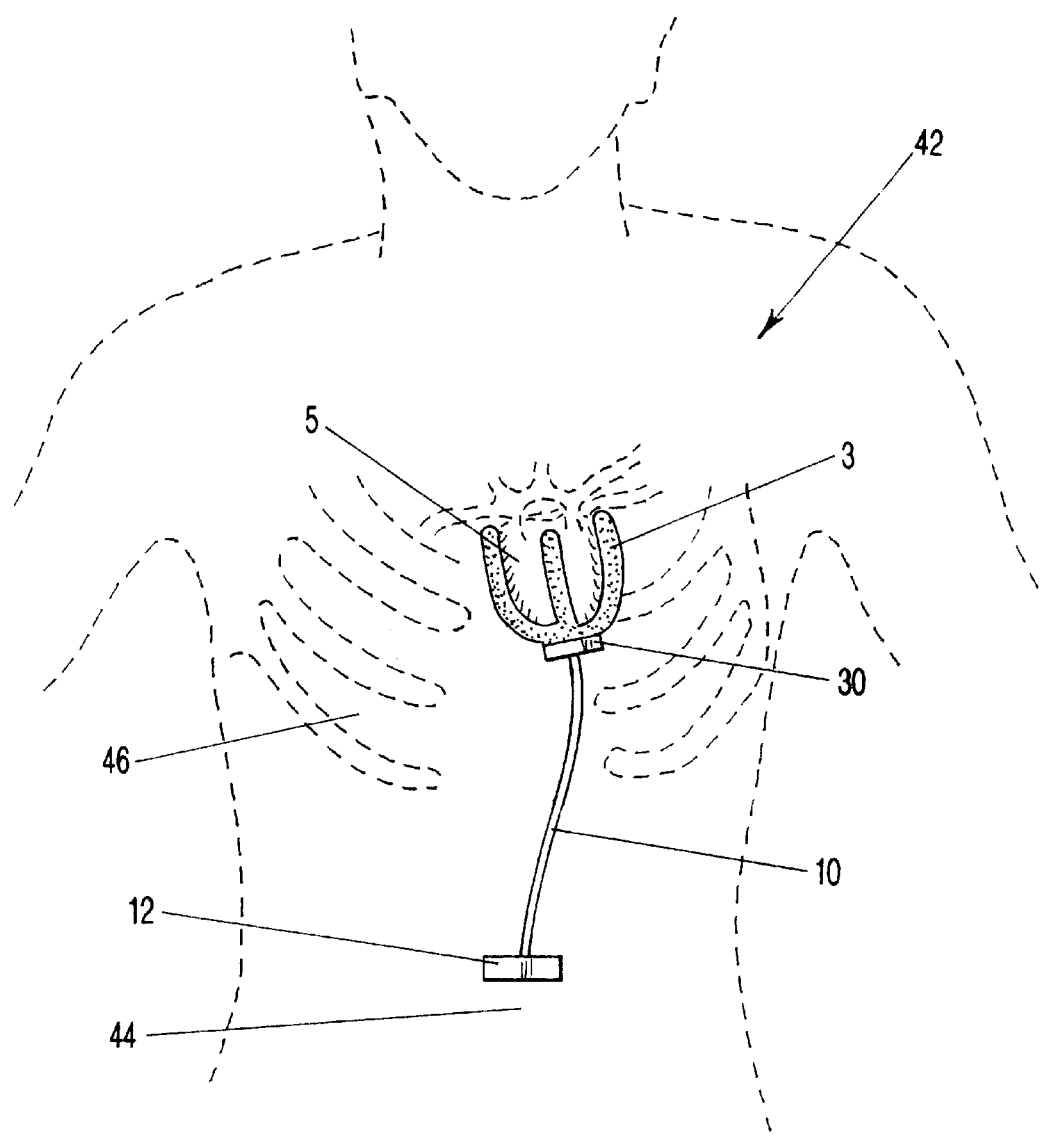
FIG. 7 illustrates the general arrangement of the invention placed inside the body of a patient.

FIG. 7 depicts the general arrangement of the compression assembly 30 implanted inside a human body 42 such that the base support assembly 12 is housed in the base of the abdomen 44 with flexible stem 10 extending to the soft compression fingers 3 and the compression assembly in the chest 46. This arrangement allows the compression assembly to perform its intelligent compression of the heart muscle 5 while maintaining a flexible undulation for the heart 5 and to allow heart 5 to make lateral motion as needed while being compressed by the soft compression fingers 3.

Figure 8A:
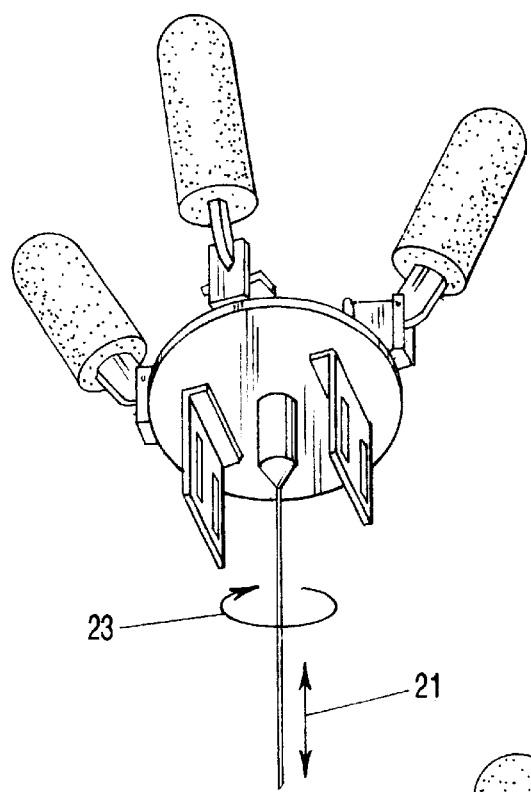
FIGS. 8(a) and (b) illustrates the combined torsional and linear robotic actuation of the compression fingers.
Figure 8B:
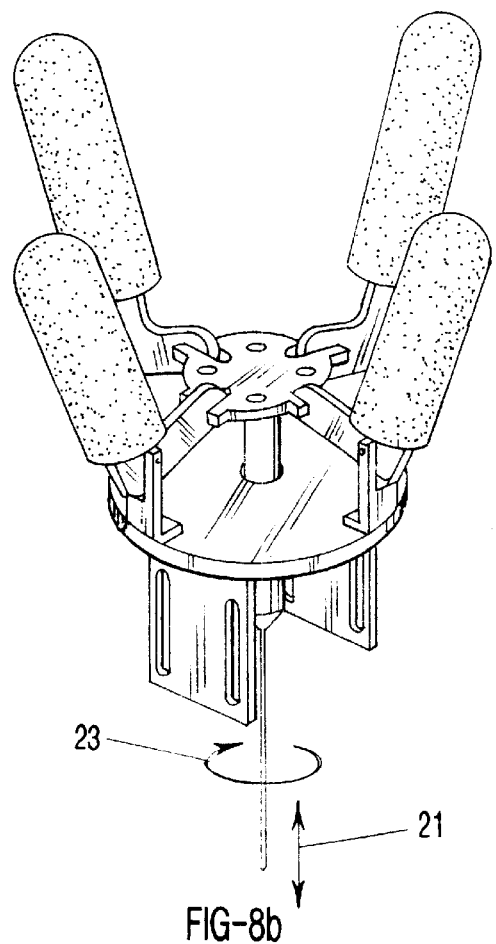

FIG. 8(a) and 8(b) depict another advantage of the proposed embodiments, in the sense that such compression embodiments allow both linear motion 21 for the compression of the heart as well as torsional motion 23 for the heart muscle, if that need arises.

Figure 9:
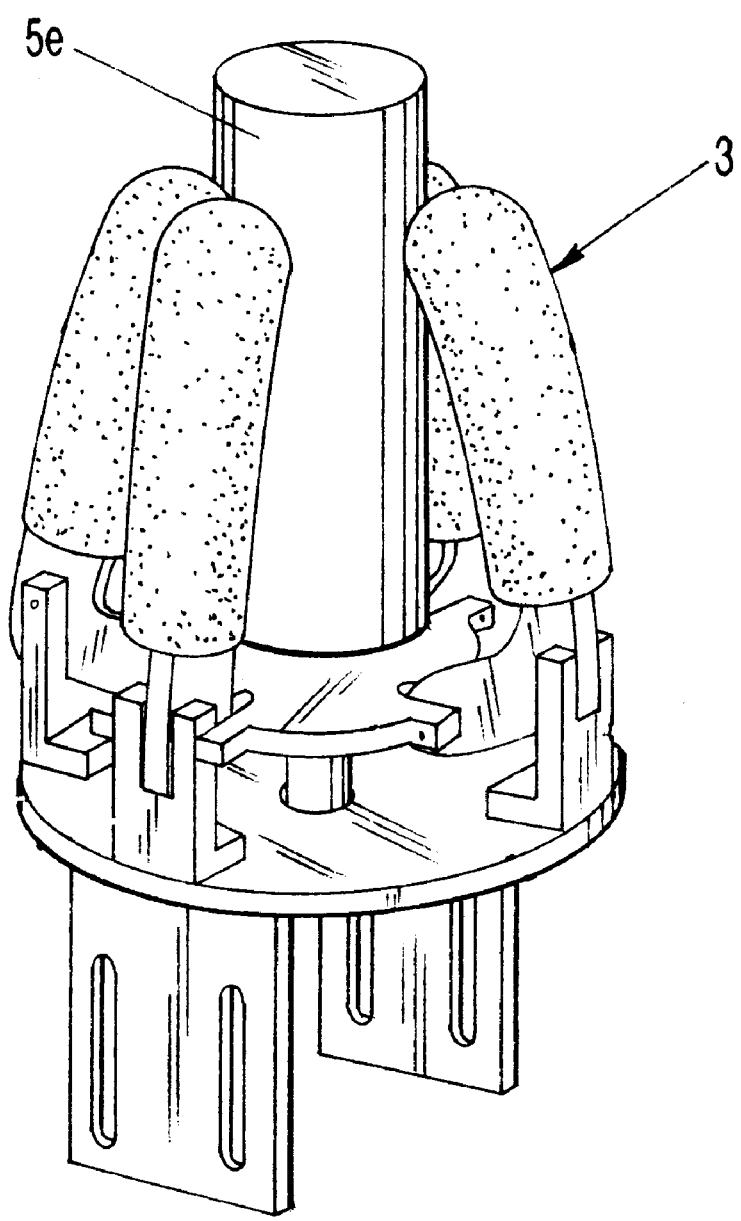
FIG. 9 depicts another embodiment of the compression fingers used as a peristaltic compression pump for the aorta.
Figure 10:
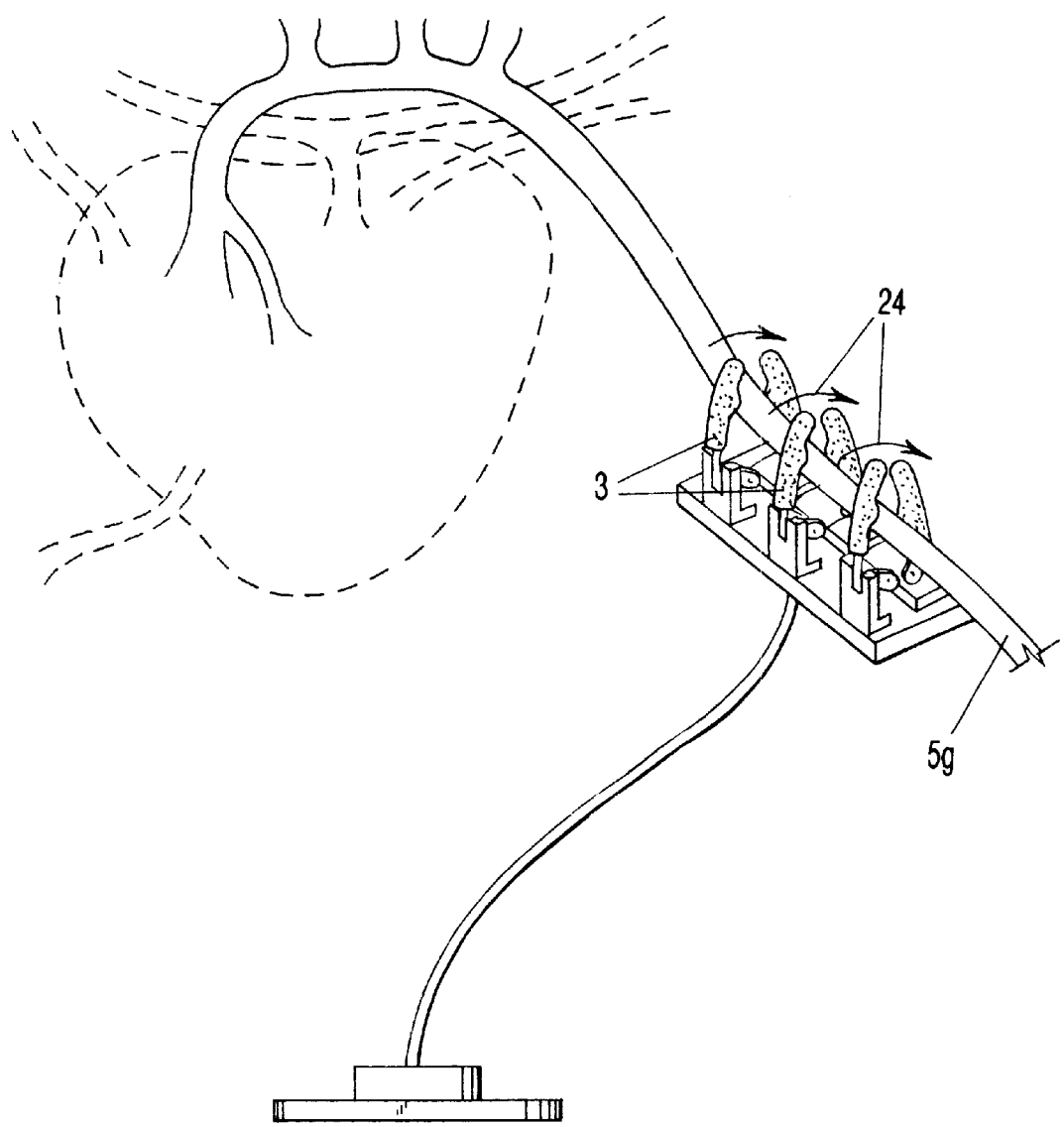
FIG. 10 illustrates the use of the invention in creating peristaltic pressure pump for the aorta to enhance blood circulation.

FIG. 9 depicts a general arrangement for the soft compression fingers 3 to compress the aorta 5(e) rather than the heart muscle 5, to create robotically controlled peristaltic compression of the aorta 5(e) to enhance blood circulation in the patient's body. FIG. 10 depicts a general configuration of a smaller version of the device with suitably arranged soft compression fingers 3 with soft covers 4 to create peristaltic compression 24 of the aorta 5(e) or descending aorta 5(g).

Referring back to FIGS. 1 and 2, in conjunction with FIG. 10, note that in operating the compression assembly 30, the robotic linear actuation mechanism 11, and the microprocessor-controlled solenoid 12 is activated by switch 12(d) such that the current generated by the battery 12(a) and supplied to the circuit 12(d) as regulated by the microprocessor 12(c) causes cable 9 to pull the central platform 7 towards the abdomen, against the base platform 1, thus causing the soft compression fingers 4 to close and compress the heart muscle 5 (systole) due to the action of resilient spring loaded collar 16. As solenoid 12 is de-energized resilient collar 16 quickly retracts the soft compression fingers 4 away from the heart muscle 5 to allow the heart muscle 5 to expand freely (diastole). As solenoid 12 is activated, the associated pressure sensors 4(a) actively communicate with the microprocessor 12(d) to exactly apply the needed pressure to the heart muscle 5 as well as sensing the rhythm so as to accelerate to decelerate the rhythm as desired. The invention thus, in operation forces blood through the associated vessels 5(a)–5(g) in a rhythm according to the pulsating current supplied through circuit 12(c). When solenoid 12 is turned off, resilient spring loaded collar 16 quickly retracts the soft compression fingers 4 away from the heart muscle 5 allowing it to expand freely (diastole). The pulsating action of the robotic linear actuator (solenoid) 12 can be optionally synchronized with the natural SA and AV nodal rhythms of the heart 5 by current supplied to the robotic linear actuator 12.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, and of the corresponding application, are hereby incorporated by reference.

What is claimed is:

1. An implantable organ compression apparatus for selectively assisting blood pumping through the organ, the apparatus comprising:

at least one finger for compressing the organ during systole releasing the organ during diastole; and a robotic actuating mechanism for actuating and releasing said at least one finger comprising an actuating cable, wherein said robotic actuating means further comprises a spring loaded apparatus for releasing said at least one finger.

2. The invention of claim 1 wherein said at least one finger comprises a soft outer cover.

3. The invention of claim 1 wherein said at least one finger further comprises at least one bump.

4. The invention of claim 1 wherein said at least one finger further comprises a pressure sensor.

5. The invention of claim 1 wherein said at least one finger further comprises a motion sensor.

6. The invention of claim 1 wherein said at least one finger further comprises a skirt.

7. The invention of claim 1 wherein said robotic actuating mechanism comprises a control apparatus.

8. The invention of claim 1 further comprises a power source.

9. The invention of claim 8 wherein said power source comprises an implantable battery.

10. The invention of claim 8 wherein said power source is transcutaneous.

11. An implantable organ compression apparatus for selectively assisting blood pumping through the organ, the apparatus comprising:

at least one finger, wherein said at least one finger is pivotally affixed to a base platform and a central platform; and a robotic actuating mechanism comprising an actuating cable for pulling said central platform towards said base platform thus causing said at least one finger to compress the organ during an actuation cycle and pushing said central platform away from said base platform thus causing said at least one finger to release the organ during a deactivation cycle.

12. The invention of claim 11 wherein said at least one finger further comprises a pressure monitoring apparatus.

13. The invention of claim 11 wherein said at least one finger further comprises a motion sensing apparatus.

14. The invention of claim 11 wherein said at least one finger further comprises at least one bump.

15. The invention of claim 11 wherein said actuating cable further comprises a flexible stem.

16. The invention of claim 11 wherein said robotic actuating mechanism further comprises a spring loaded collar for pushing said central platform away from said base platform.

17. The invention of claim 1 further comprising a base support for actuating said actuating cable configured to be housed in the base of the abdomen.

18. The invention of claim 1 further comprising a flexible stem encasing said actuating cable.

* * * * *